(12) United States Patent
Klumpen

(10) Patent No.: US 9,586,737 B2
(45) Date of Patent: Mar. 7, 2017

(54) ELASTOMERIC CLOSURE WITH BARRIER LAYER AND METHOD FOR ITS MANUFACTURE

(75) Inventor: Thomas Klumpen, Zuelpich-Loevenich (DE)

(73) Assignee: West Pharmaceutical Services Deutschland GmbH & Co. KG, Eschweiler (DE)

( * ) Notice: Subject to any disclaimer, the term of this patent is extended or adjusted under 35 U.S.C. 154(b) by 0 days.

(21) Appl. No.: 13/500,562

(22) PCT Filed: Oct. 12, 2010

(86) PCT No.: PCT/US2010/052262
§ 371 (c)(1),
(2), (4) Date: Apr. 5, 2012

(87) PCT Pub. No.: WO2011/044569
PCT Pub. Date: Apr. 14, 2011

(65) Prior Publication Data
US 2012/0205374 A1    Aug. 16, 2012

Related U.S. Application Data

(60) Provisional application No. 61/250,251, filed on Oct. 9, 2009.

(51) Int. Cl.
*B65D 39/00* (2006.01)
*B65D 39/02* (2006.01)
(Continued)

(52) U.S. Cl.
CPC .......... *B65D 51/002* (2013.01); *A61J 1/1406* (2013.01); *A61M 5/31511* (2013.01);
(Continued)

(58) Field of Classification Search
CPC .. B65D 51/002; B65D 39/0052; B65D 39/02; A61M 5/31511; A61M 2005/3104; A61J 1/1406
See application file for complete search history.

(56) References Cited

U.S. PATENT DOCUMENTS 4,452,007 A * 6/1984 Martin ............................ 446/45
5,288,560 A * 2/1994 Sudo ................... A61M 5/31511
215/364

(Continued)

FOREIGN PATENT DOCUMENTS

JP          7255821 A    10/1995
JP       2004180859 A    7/2004
(Continued)

OTHER PUBLICATIONS

Int'l Preliminary Report on Patentability issued Apr. 19, 2012 in Int'l Application No. PCT/US2010/052262.

(Continued)

*Primary Examiner* — Kevin R Kruer
(74) *Attorney, Agent, or Firm* — Panitch Schwarze Belisario & Nadel LLP

(57) ABSTRACT

An elastomeric closure (10) having an internal barrier film (16) is provided. The elastomeric closure includes a top portion (12) and a bottom portion (14) formed together with a barrier film (16) disposed between the top and bottom portions. The barrier film may span the overall length and width of the elastomeric closure and preferably includes an aluminum foil as the barrier film material.

18 Claims, 8 Drawing Sheets

(51) Int. Cl.
*B65D 51/00* (2006.01)
*A61M 5/315* (2006.01)
*A61J 1/14* (2006.01)
*A61M 5/31* (2006.01)

(52) U.S. Cl.
CPC ......... *B65D 39/0052* (2013.01); *B65D 39/02* (2013.01); *A61M 2005/3104* (2013.01)

(56) References Cited

U.S. PATENT DOCUMENTS

| | | | | |
|---|---|---|---|---|
| 5,484,566 | A * | 1/1996 | Gabbard | B29C 43/146 264/250 |
| 6,165,402 | A * | 12/2000 | Gabbard | B29C 43/021 264/255 |
| 8,334,869 | B1 * | 12/2012 | Padmakar et al. | 345/420 |
| 8,404,352 | B2 * | 3/2013 | Schwab et al. | 428/476.9 |
| 2007/0269624 | A1 * | 11/2007 | Granger | 428/36.7 |

FOREIGN PATENT DOCUMENTS

| | | |
|---|---|---|
| JP | 2004305307 A | 11/2004 |
| WO | 2009121086 A1 | 10/2009 |
| WO | 2009151129 A1 | 12/2009 |

OTHER PUBLICATIONS

International Search Report issued Jan. 18, 2011 in Int'l Application No. PCT/US2010/052262.

Int'l Preliminary Examination Report issued May 10, 2012 in Int'l Application No. PCT/US2010/052262.

Office Action issued Feb. 24, 2014 in CN Application No. 201080045596.7.

Office Action issued Aug. 22, 2014 in CN Application No. 201080045596.7.

* cited by examiner

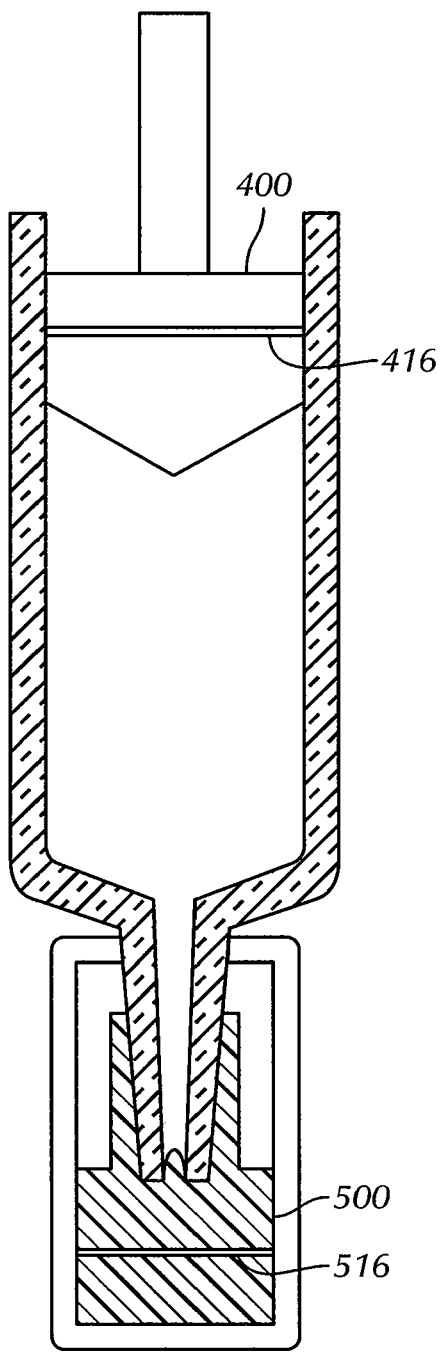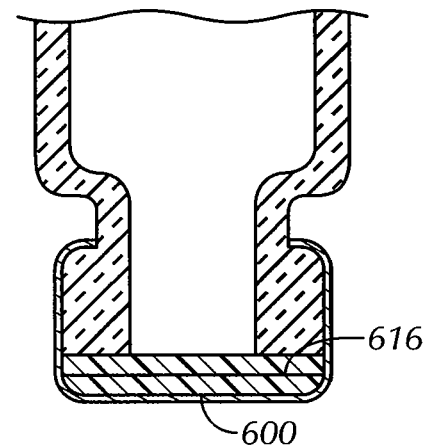
*FIG. 16*
*FIG. 15*

ELASTOMERIC CLOSURE WITH BARRIER LAYER AND METHOD FOR ITS MANUFACTURE

CROSS-REFERENCE TO RELATED APPLICATION

This application is a section 371 of International Application No. PCT/US2010/052262, filed Oct. 12, 2010, which was published in the English language on Apr. 14, 2011 under International Publication No. WO 2011/044569 which claims the benefit of U.S. Provisional Patent Application No. 61/250,251, filed Oct. 9, 2009, the disclosures of which are incorporated herein by reference.

BACKGROUND OF THE INVENTION

The present invention relates generally to an elastomeric closure having a barrier film layer. In particular, the present invention relates to an elastomeric closure having a barrier film layered internally of the elastomeric closure.

Elastomeric closures are generally used as sealing devices for vials, medical vessels, instruments, syringes, etc. For a closure material of a medicament vessel, it is generally required that the material have heat resistance, compression strain resistance, be chemically inert, and have a low permeability to gases and water vapor. In this respect, elastomers, which have excellent sealing properties, are often used for closure materials for medicament vessels. However, conventional elastomers, while generally having low permeability, still suffer from the permeation and transmission of gases, such as water vapor and oxygen. The transmission of water vapor through elastomeric closures have become of greater concern in today's medical field due to the ever increasing sensitivity of drugs, such as lyophilized and modern biotech drugs and other moisture sensitive products stored in such medicament vessels over extended periods of time, such as several years. Lyophilized and biotech drugs are highly sensitive to even very low levels of water and therefore, a moisture barrier closure is required. Such exposure to water for lyophilized and biotech drugs can adversely effect the performance and stability of the drugs. The problems associated with water vapor transmission are further aggravated when lyophilized or biotech drugs are stored for extended periods of time during shelf life. The shelf life of such drugs itself may be limited due to the effects of water vapor transmission into the drug's container.

Accordingly, a need still exists for an elastomeric closure that can sufficiently seal a vessel or device and provide a barrier to the transmission of water vapor and/or oxygen and other fluids through the closure without introducing the barrier material as a secondary source of contamination for the vessel or its contents.

BRIEF SUMMARY OF THE INVENTION

In accordance with the present invention, the water vapor and/or gas vapor transmission problem of elastomeric closures is solved by engendering a barrier film layer internal to the elastomeric closure, and preferably one that spans the entire width of the closure. In this way, the barrier film layer not only provides a barrier to the transmission of water vapor and/or gases through the elastomeric closure, but also prevents the barrier film layer from serving as a secondary source of contaminates for the internal contents of a vessel or device used in conjunction with the elastomeric closure.

In a first preferred embodiment, the present invention provides an elastomeric closure that includes a top portion, a bottom portion and a barrier film. The top portion includes a bottom surface and the bottom portion includes a top surface in facing engagement with the bottom surface of the top portion. The barrier film is located between the bottom surface of the top portion and the top surface of the bottom portion.

In a first aspect, the present invention provides a method of manufacturing an elastomeric closure having a top portion, a bottom portion, and a barrier film located between the top portion and the bottom portion. The method includes the steps plasma treating a top surface and bottom surface of the barrier film to increase its surface energy, and then layering the plasma treated barrier film on a first layer of uncured elastomer. The method further includes the steps of hot pressing and vulcanizing the plasma treated barrier film and the first layer of uncured elastomer together to form the bottom portion of the elastomeric closure bonded to the plasma treated barrier film, and hot pressing and vulcanizing the bottom portion of the elastomeric closure bonded to the plasma treated barrier film to a second layer of uncured elastomer to form a top portion of the elastomeric closure bonded to the plasma treated barrier film.

In a second aspect, the present invention provides a method of manufacturing an elastomeric closure having a top portion, a bottom portion, and a barrier film located between the top portion and the bottom portion. The method includes the steps of forming a first bonding layer and a second bonding layer on the barrier film, and then layering the barrier film on a first layer of uncured elastomer. The method further includes the steps hot pressing and vulcanizing the barrier film and the first layer of uncured elastomer together to form the bottom portion of the elastomeric closure bonded to the barrier film, and hot pressing and vulcanizing the bottom portion of the elastomeric closure bonded to the barrier film to a second layer of uncured elastomer to form a top portion of the elastomeric closure bonded to the barrier film.

In a third aspect, the present invention provides a method of manufacturing an elastomeric closure having a top portion, a bottom portion, and a barrier film located between the top portion and the bottom portion. The method includes the steps of mixing uncured elastomer with an adhesion promoter, and then layering the barrier film on a first layer of uncured elastomer with adhesion promoter. The method further includes the steps hot pressing and vulcanizing the barrier film and the first layer of uncured elastomer with adhesion promoter together to form the bottom portion of the elastomeric closure bonded to the barrier film, and hot pressing and vulcanizing the bottom portion of the elastomeric closure bonded to the barrier film to a second layer of uncured elastomer with adhesion promoter to form a top portion of the elastomeric closure bonded to the barrier film.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 15 is a partial, cross-sectional, elevational view of a syringe with a plunger and tip cap in accordance with another preferred embodiment of the present invention; and FIG. 16 is a partial, cross-sectional, elevational view of a sealing disk in accordance with yet another preferred embodiment of the present invention.

DETAILED DESCRIPTION OF THE INVENTION

Reference will now be made in detail to the present embodiments of the invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. Such directional terms used in conjunction with the following description of the drawings should not be construed to limit the scope of the invention in any manner not explicitly set forth. Unless specifically set forth herein, the terms "a", "an" and "the" are not limited to one element but instead should be read as meaning "at least one." The terminology includes the words noted above, derivatives thereof and words of similar import.

Figure 1:
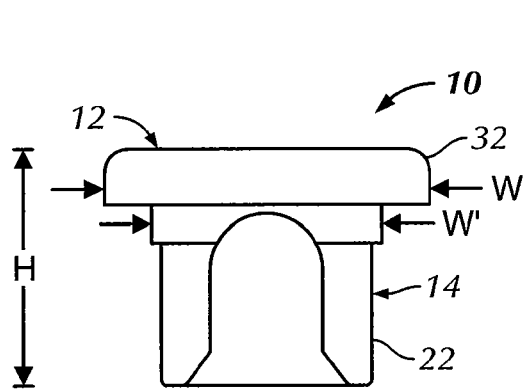
FIG. 1 is a front-side, elevational view of an elastomeric closure in accordance with a preferred embodiment of the present invention.
Figure 2:
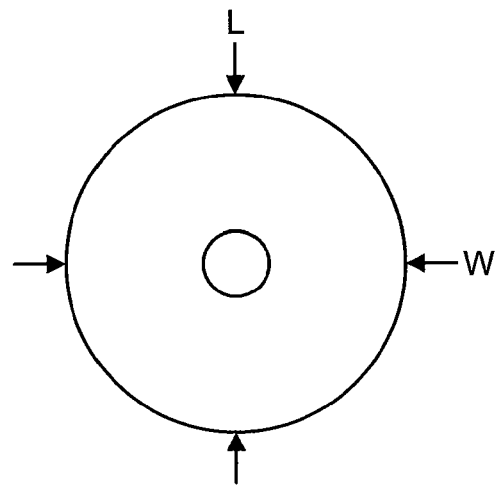
FIG. 2 is a top plan view of the elastomeric closure of FIG. 1.
Figure 3:
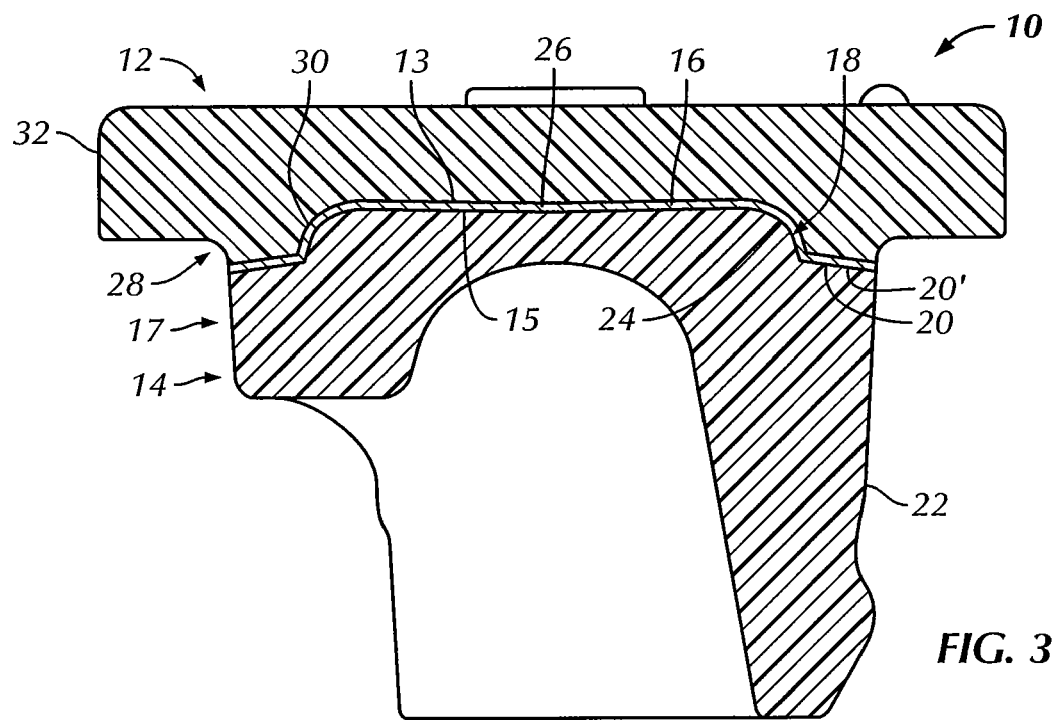
FIG. 3 is an enlarged, side, cross-sectional, elevational view of the elastomeric closure of FIG. 1.
Figure 4:
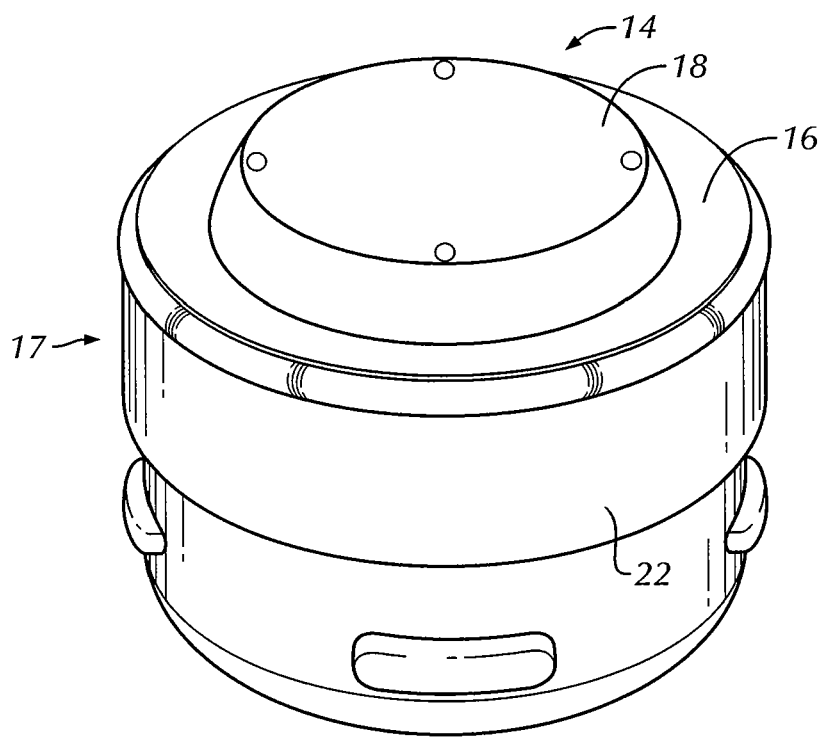
FIG. 4 is an enlarged top, rear, perspective view of a bottom portion of the elastomeric closure of FIG. 1 with a barrier film.
Figure 10:
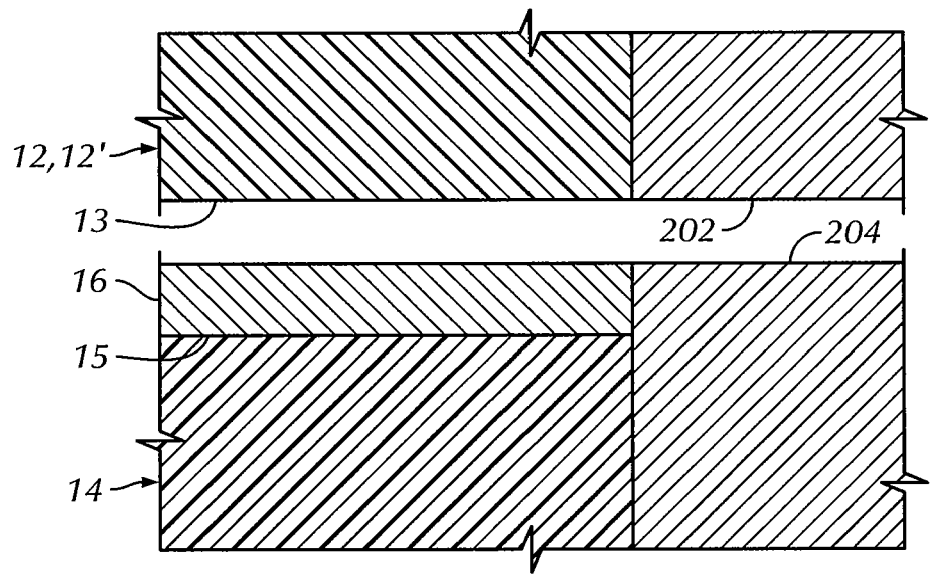
FIG. 10 is an enlarged, schematic, partial, side, cross-sectional, elevational view of a bottom portion of the elastomeric closure of FIG. 9 and another layer of elastomer within a top mold cavity for forming a top portion of the elastomeric closure of FIG. 3.

In accordance with a first preferred embodiment, the present invention provides for an elastomeric closure 10, as shown in FIGS. 1-4. Referring to FIGS. 3 and 4, the elastomeric closure 10 includes a top portion 12, a bottom portion 14 and a barrier film 16 located between the top portion 12 and the bottom portion 14. The top portion 12 and bottom portion 14, in combination, substantially form the elastomeric closure 10 for a device or vessel, such as a medicament vessel, vial or syringe plunger. The configuration of the elastomeric closure 10 can be of any conventional closure, such as a NovaPure™ closure stopper or Westar® RU stopper by West Pharmaceutical Services, Inc. of Lionville, Pa., a syringe piston 400, a syringe tip cap 500, a sealing disk 600 (FIGS. 10 and 11) or any other elastomeric closure for conventional vials, evacuated blood collection tubes and the like. In general, the present invention can be applied to any elastomeric closure configuration for any type of vessel system or device that requires a vapor and fluid tight seal to be maintained.

For exemplary purposes only, and not by way of limitation, the present invention will now be further described with reference to an elastomeric closure stopper 10 configured similar to a NovaPure™ closure, as shown in FIGS. 1 and 2. The elastomeric closure 10 includes a length "L", a width "W" and a height "H". The width W is the overall width of the elastomeric closure stopper 10. A width W' is the width of the elastomeric closure along the bottom portion 14 (or annular leg portion).

In applying the present invention to any elastomeric closure configuration, the top portion 12 can be any upper section of the elastomeric closure sectioned off about a generally horizontal plane, whereas the bottom portion 14 is the remainder of the elastomeric closure, or vice versa. As best shown in FIG. 3, the top portion 12 is defined by or separated from the bottom portion 14 by the barrier film 16.

In general, the elastomeric closure 10 includes a top portion 12 having a bottom surface 13 and a bottom portion 14 having a top surface 15 in facing engagement with the bottom surface 13 of the top portion 12, as shown, for example, in FIG. 3. Additionally, the barrier film 16 is located between the bottom surface 13 of the top portion 12 and the top surface 15 of the bottom portion 14.

The elastomeric material used for the elastomeric closure can be, for example, a synthetic or natural rubber, such as butyl rubber, isoprene rubber, butadiene rubber, halogenated butyl rubber (e.g., bromobutyl rubber), ethylene propylene terpolymer, silicone rubber, combinations thereof and the like.

Preferably, the bottom portion 14 is configured with an upper section 17 (i.e., a proximal end of the bottom portion 14) that includes a center portion 18 concentric about the lower sides 22 of the elastomeric closure 10 and an outer flange or sloped region 20 that circumscribes the center portion 18. The center portion 18 has a diameter preferably at least 50% of the overall diameter of the bottom portion 14 and extends proud of the outer flange/sloped region 20. That is, the center portion 18 is an upper region 18 of the bottom portion 14 that is preferably frustum shaped. The outer flange/sloped region 20 can be configured as a generally horizontal surface or an angled surface 20' that slopes outwardly and downwardly, as shown in FIG. 3. Preferably, the angled surface 20' slopes from about 2 to 25 degrees and more preferably from about 5 to 15 degrees. The center portion 18 can also be configured with a rounded edge 24 leading from an upper surface 26 of the center portion 18 to the outer flange/sloped region 20.

The top portion 12 includes a lower section or a lower region 28 that includes a bottom surface geometry that generally compliments and mates with the configuration of the upper section 17 and upper region 18 of the bottom portion 14. In particular, the lower section 28 includes a recess 30 concentric about the upper sides 32 of the elastomeric closure stopper 10. The recess 30 is configured with a depth and a diameter that generally compliments and mates with the frustum shaped center portion 18 of the bottom portion 14.

In general, the lower section 28 of the top portion 12 is configured as a female end that compliments and mates with the upper section 17 of the bottom portion 14 configured as a male end. The male and female ends of the top and bottom portions 12, 14 advantageously provide for improved structural strength and manufacturability when the top portion 12 and bottom portion 14 are secured and sealed together, as further described below.

Alternatively, the bottom portion 14 can be configured as a female end and the top portion 12 configured as a male end. In addition, besides a generally frustum shaped center portion 18 and complementary frustum shaped recess 30, the lower section 28 and upper section 17 can be configured with any male and female ends, interlocking ends, or engaging ends to provide a more advantageous interlock between the top and bottom portions 12, 14. For example, the upper region 18 can be configured as a cylindrical, pyramidal or annular shape, while the lower region 28 of the top portion 12 is complimentarily shaped.

The barrier film 16 is configured to be located between the top portion 12 and bottom portion 14 of the elastomeric closure 10. The barrier film 16 extends or spans completely or almost completely (i.e., partially) across the top surface 15 of the bottom portion 14 (FIG. 4) and/or across the bottom surface 13 of the top portion 12 (FIG. 3). That is, the barrier film 16 spans completely or substantially completely across the entire width and length that divides the top and bottom portions 12, 14 of the elastomeric closure 10.

Figure 5:
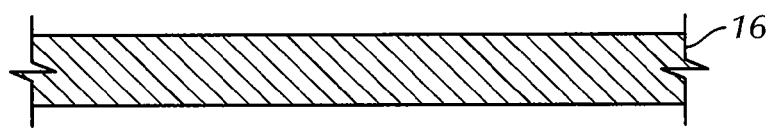
FIG. 5 is a schematic, partial, side elevational view of a barrier film applicable to the elastomeric closure of FIG. 3.

The barrier film 16 (FIG. 5) can be any barrier material suitable for its intended use, and preferably a barrier film material having a low water vapor and/or oxygen (i.e., fluids) transmission rate. Suitable barrier materials can include, but are not limited to, a metallic foil, such as aluminum foil or stainless steel foil, a polyester film, a polyamide film, a polyvinylchloride film, halogenated polymer films, non-halogenated polyisobutylene-isoprene rubber films, polyvinylidene chloride (PVDC) films, cyclic olefin copolymer (COC) films, polypropylene films, polyethylene films, polytetrafluoroethylene (PTFE) films, polychlorotrifluoroethylene (PCTFE) films (such as Aclar® from Honeywell International Inc. of Morristown, N.J.), silicone oxide (SiOx) coated polymer films, and/or combinations thereof. Additional barrier film materials can also include polyvinyl chloride (PVC) and polyester films that are partially covered with silicon oxide and/or aluminum oxide.

Preferably, the barrier film 16 is a barrier film having a very low water vapor transmission and/or oxygen transmission rate, such as an aluminum foil film. Aluminum foil is an excellent barrier to water vapor transmission with reported water vapor transmission rates as low as 0.001 g/m²/day. Preferably, the barrier film 16 has a thickness of about 0.01 mm to 1.0 mm, but could be of some lesser or greater thickness in some applications.

The barrier film 16 can be directly bonded to the top and bottom portions 12, 14 of the elastomeric closure 10 or alternatively bonded thereto with the use of additional bonding layers 102, 102'. The bonding layers 102, 102' are layered between the barrier film 16 and the opposing surfaces of the top portion 12 and the bottom portion 14. The bonding layers 102, 102' provide a means to enhance the bonding strength between the barrier film 16 and the top and bottom portions 12, 14 of the elastomeric closure 10.

The bonding layers 102, 102' can be an organic material layer or an inorganic material layer. Preferred exemplary bonding layer materials include an epoxy, an adhesive primer, a silane compound or a resin/silicone based primer, e.g., Elastobond 11, Elastobond 24 and Elastobond 56 from Avokal GmbH of Wuppertal Germany, and HV Primer from Dow Corning of Midland, Mich., or a deposition layer formed from $SiO_2$, $Al_2O_3$, or diamond-like carbon.

Instead of bonding layers, the elastomeric closure 10 can alternatively be configured to include an adhesion promoter, such as, a silane compound, an epoxy, a polymer resin, an adhesive and primers, e.g., silane based adhesives MEGUM™ from Chemetall, ROBOND™ from Dow Corning of Midland, Mich., and THIXON™ from Morton, and CHEMOSIL® from Chemlok and Henckel, for promoting bonding between the barrier film 16 and the top and bottom portions 12, 14 of the elastomeric closure 10. The adhesion promoter is mixed and/or compounded with the uncured elastomeric resin used to mold the top and bottom portions 12, 14 of the elastomeric closure 10. The application of adhesion promoters within the uncured elastomer resin used to mold the elastomeric closure 10 advantageously allows for improved bonding between the barrier film 16 and the surfaces of the elastomeric closure 10 to which it is bonded to. Additional adhesion promoters applicable to the present invention are disclosed in U.S. Pat. Nos. 7,807,015 and 6,759,129, the disclosures of which are hereby incorporated by reference herein in its entirety.

Figure 7:
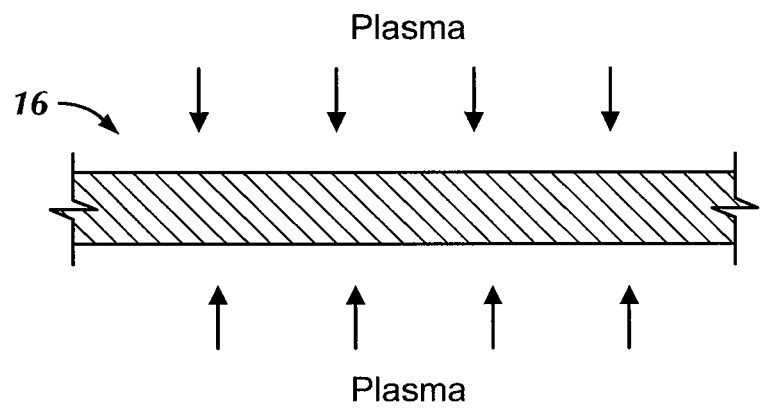
FIG. 7 is a schematic, partial, side elevational view of a barrier film applicable to the elastomeric closure of FIG. 3 that is plasma treated.
Figure 8:
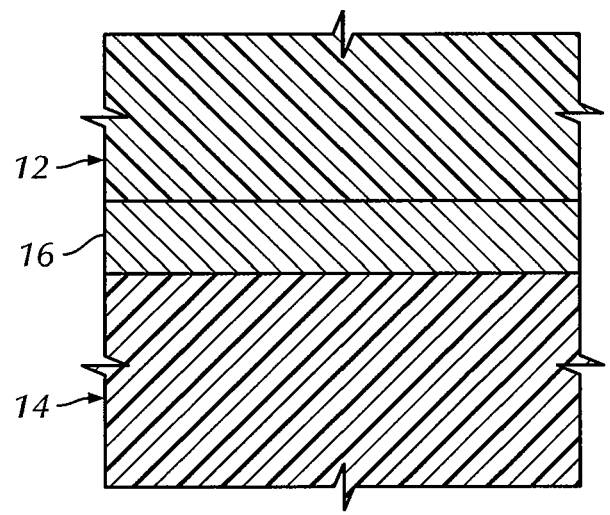
FIG. 8 is an enlarged, schematic, partial, side, cross-sectional, elevational view of the barrier film of FIG. 7 layered within the elastomeric closure of FIG. 3.

By way of example only, and not by way of limitation, methods of manufacturing the elastomeric closure 10 having a barrier film 16 of the present invention will now be described. In a first aspect of the instant invention, the present method has been developed to form the elastomeric closure 10, wherein the top portion 12 and the bottom portion 14 are directly bonded to the barrier film 16. In a first step (FIG. 7), the barrier film 16 is plasma treated on both its upper and lower surfaces to form a plasma activated barrier film surface. The plasma treatment results in structural modifications to the surfaces of the barrier film 16 resulting in e.g., high surface energy and wetting of the barrier film's surfaces. As a result, the plasma treated barrier film 16 can more effectively be bonded to the surfaces of the top and bottom portions 12, 14 (FIG. 8) of the elastomeric closure 10 by, e.g., hot pressing and vulcanizing. Such plasma treatment methods for treating barrier films are known in the art and a detailed description of their structure, operation and function is not necessary for a complete understanding of the present invention. However, exemplary plasma treatment methods include Openair® plasma by Plasmatreat of Elgin, Ill., $CF_4$ Plasma, and Interface or Oxygen Plasma.

In the next steps (FIG. 9), the plasma treated barrier film 16 is layered on top of a first layer of uncured elastomer 14' within a bottom mold 200. The barrier film 16 and first layer of uncured elastomer 14' is then hot pressed and vulcanized to form the bottom portion 14 bonded to the barrier film 16.

The time, heat and pressure for hot pressing the bottom portion 14 to the barrier film will depend upon the specific elastomeric material used to form the bottom portion 14. Generally speaking, elastomeric materials and compression molding processes are known in the art and a detailed description of the compression molding processes' time, temperature and pressure specifications is not necessary for a complete understanding of the present invention. An exemplary compression molding process applicable to the present invention is disclosed in U.S. Pat. No. 5,078,941, the disclosure of which is hereby incorporated by reference herein in its entirety. However, the hot pressing and vulcanizing is conducted preferably at temperatures of about 140 to 220 degrees Celsius and pressures of about 40 to 70 kg/cm$^2$ for about 2 to 15 minutes.

In the final steps (FIG. 10), a second layer of uncured elastomer 12' is assembled within a top mold 202 and the already formed bottom portion 14 with barrier film 16 is placed in another mold 204 after trimming. The second layer of uncured elastomer 12' is then hot pressed and vulcanized against the exposed surface of the barrier film 16 situated within the mold 204, thus forming a unitary structure of a top portion 12 bonded to the barrier film 16 and the bottom portion 14. The hot pressing and vulcanizing is conducted preferably at temperatures of about 140 to 220 degrees Celsius and pressures of about 40 to 70 kg/cm$^2$ for about 2 to 15 minutes.

Figure 6:
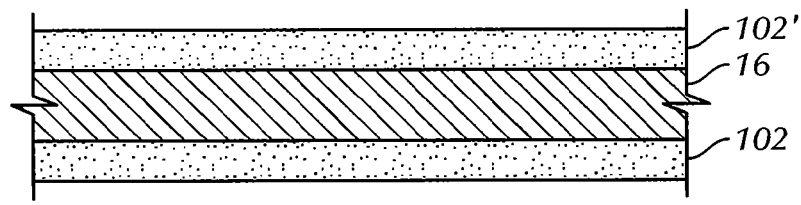
FIG. 6 is a schematic, partial, side elevational view of a barrier film having bonding layers on both its top and bottom surfaces applicable to the elastomeric closure of FIG. 3, in accordance with another aspect of the present invention.

In a second aspect of the instant invention, the present method has been developed to form the elastomeric closure 10, wherein the top portion 12 and the bottom portion 14 are bonded to the barrier film 16 via bonding layer 102, 102'. In a first step (FIG. 6), the barrier film 16 is formed with the first bonding layer 102 on a bottom surface of the barrier film 16 and a second bonding layer 102' formed a top surface of the barrier film 16. The bonding layers 102, 102' can be any suitable bonding agent/material that bonds the barrier film 16 to the top and bottom portions 12, 14 and provides the necessary bonding strength. Preferably, the bonding layers 102, 102' are an epoxy, an adhesive primer, a silane or a silicone based primer, e.g., Elastobond 11, Elastobond 24 and Elastobond 56 from Abokol Heller and HV Primer from Dow Corning of Midland, Mich., or a deposition layer formed from SiO$_2$, Al$_2$O$_3$, or an organic material, such as diamond-like carbon.

Such bonding layers 102, 102' can be applied to the barrier film 16 by e.g., dip coating, curtain coating, spray coating, chemical deposition, physical deposition and the like. Such techniques for coating films with bonding layers are known in the art, as such, a detailed description of such processes is not necessary for a complete understanding of the present invention.

Figure 11:
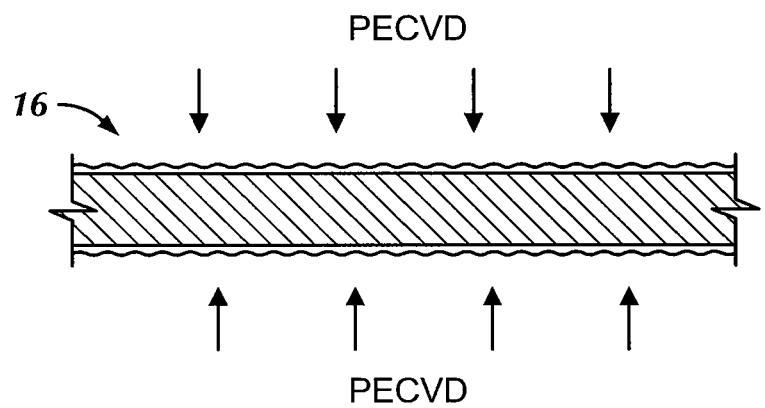
FIG. 11 is a schematic, partial, side elevational view of a barrier film applicable to the elastomeric closure of FIG. 3 that is treated with plasma enhanced chemical vapor deposition.

However, plasma enhanced chemical vapor deposition is a preferred method of coating the barrier film 16 with bonding layers 102, 102' formed as a deposition layer composed of SiO$_2$, Al$_2$O$_3$, or an organic material, such as diamond-like carbon (FIG. 11).

Figure 12:
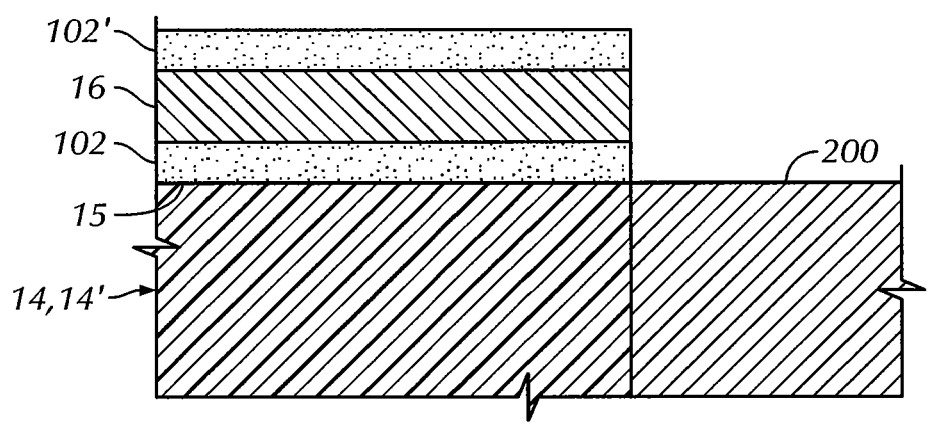
FIG. 12 is an enlarged, schematic, partial, side, cross-sectional, elevational view of a bottom portion of the elastomeric closure of FIG. 3 in a bottom cavity mold layered with a barrier film having bonding layers.

In the next steps (FIG. 12), the barrier film 16 with bonding layers 102, 102' is then layered on top of a first layer of uncured elastomer 14' within a bottom mold 200. The barrier film 16 and first layer of uncured elastomer 14' is then hot pressed and vulcanized to form the bottom portion 14 bonded to the barrier film 16. The time, heat and pressure for hot pressing the bottom portion 14 to the barrier film 16 is similar to the method described above in the first aspect of the invention. However, the hot pressing and vulcanizing is conducted preferably at temperatures of about 140 to 220 degrees Celsius and pressures of about 40 to 70 kg/cm$^2$ for about 2 to 15 minutes.

Figure 13:
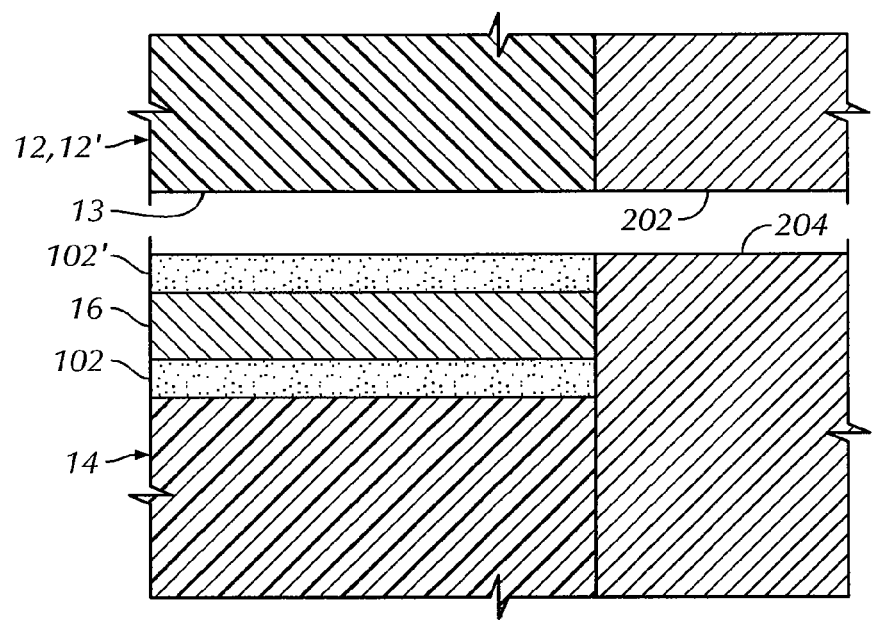
FIG. 13 is an enlarged, schematic, partial, side, cross-sectional, elevational view of a bottom portion of the elastomeric closure of FIG. 12 and another layer of elastomer within a top mold cavity for forming a top portion of the elastomeric closure of FIG. 3.

In the final steps (FIG. 13), a second layer of uncured elastomer 12' is assembled within a top mold 202 and the already formed bottom portion 14 with barrier film 16 is placed in another mold 204 after trimming. The second layer of uncured elastomer 12' is then hot pressed and vulcanized against the exposed surface of the barrier film 16 situated within the mold 204, thus forming a unitary structure of a top portion 12 bonded to the barrier film 16 and the bottom portion 14. The hot pressing and vulcanizing is conducted preferably at temperatures of about 140 to 220 degrees Celsius and pressures of about 40 to 70 kg/cm$^2$ for about 2 to 15 minutes.

Figure 14:
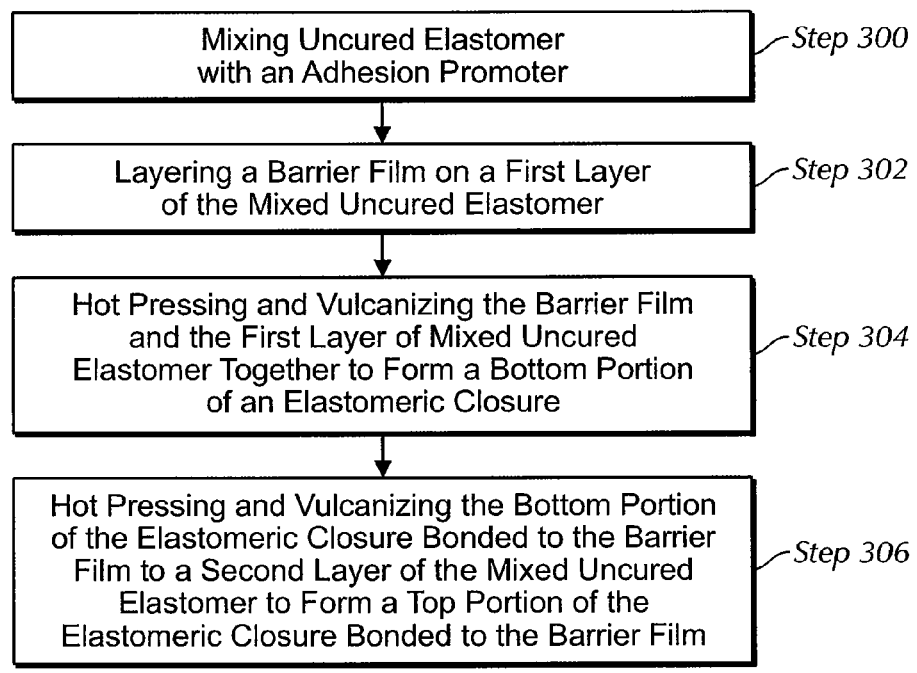
FIG. 14 is a schematic flow chart of a method of manufacturing the elastomeric closure of FIG. 1 in accordance with another aspect of the present invention.

In a third aspect of the instant invention, the present method has been developed to form the elastomeric closure 10, wherein the top portion 12 and the bottom portion 14 are bonded directly to the barrier film 16. In a first step (Step 300, see FIG. 14), the uncured elastomer used to from the elastomeric closure 10 is mixed/compounded with an adhesion promoter. The adhesion promoter can be, e.g., a silane compound, an epoxy, a polymer resin or an adhesive.

Figure 9:
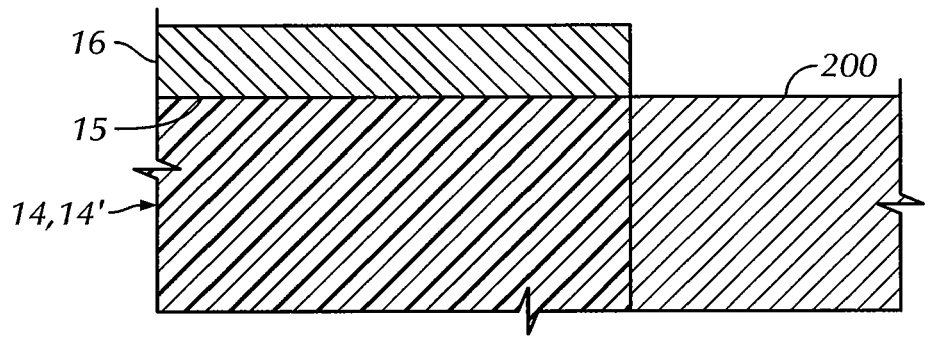
FIG. 9 is an enlarged, schematic, partial, side, cross-sectional, elevational view of a bottom portion of the elastomeric closure of FIG. 3 in a bottom cavity mold layered with a barrier film applicable to the present invention.

In the next steps, the barrier film 16 is then layered on top of a first layer of uncured elastomer 14' with adhesion promoter within a bottom mold 200 (Step 302, see FIG. 9). The barrier film 16 and first layer of uncured elastomer 14' with adhesion promoter is then hot pressed and vulcanized to form the bottom portion 14 bonded to the barrier film 16 (Step 304). The time, heat and pressure for hot pressing the bottom portion 14 to the barrier film 16 is similar to the method described above in the first aspect of the invention. However, the hot pressing and vulcanizing is conducted preferably at temperatures of about 140 to 220 degrees Celsius and pressures of about 40 to 70 kg/cm$^2$ for about 2 to 15 minutes.

In the final steps (Step 306, see FIG. 10), a second layer of uncured elastomer 12' with adhesion promoter is assembled within a top mold 202, and the already formed bottom portion 14 with barrier film 16 is placed in another mold 204 after trimming. The second layer of uncured elastomer 12' with adhesion promoter is then hot pressed and vulcanized against the exposed surface of the barrier film 16 situated within the mold 204, thus forming a unitary structure of a top portion 12 bonded to the barrier film 16 and the bottom portion 14. The hot pressing and vulcanizing is conducted preferably at temperatures of about 140 to 220 degrees Celsius and pressures of about 40 to 70 kg/cm$^2$ for about 2 to 15 minutes.

The elastomeric closure 10, as described in the above embodiments, advantageously provide for a barrier film 16 within the elastomeric closure 10. The elastomeric closure 10 with the internal barrier film 16 advantageously minimizes the total area where water vapor or gases can transmit or diffuse through the elastomeric closure 10. Furthermore, the present invention advantageously provides for an elastomeric closure 10 with a barrier film 16 that does not come in direct contact with the contents of a vessel, such as lyophilized drugs. That is, the present invention eliminates the barrier film material as an additional source of potential contaminants above and beyond that of the elastomeric material itself. In other words, the elastomeric portions of the elastomeric closure 10 completely encapsulates the barrier film 16, or is flush with the exposed surfaces of the barrier film 16. Such an internal barrier film 16 also provides for a seamless transition for users of the closures, as the elastomeric closure 10 with the internal barrier film 16 appears essentially the same as elastomeric closures without an internal barrier film 16. In other words, the barrier film 16 is not readily visible to a user. Moreover, a barrier film 16, and especially a barrier film 16 of a metallic barrier material, is not susceptible to problematic fragmentation or debris caused by needle penetration or needle coring, as the barrier film 16 would be completely or substantially completely surrounded by elastomer on both sides of the barrier film 16. Additionally, such elastomeric closures 10 with a barrier film 16 provide the ability to increase the shelf life of moisture sensitive drugs, thereby providing added value to consumers and manufacturers.

The present methods of applying a barrier film 16 internally to an elastomeric component can also be applied to numerous other elastomeric devices as well. For example, the barrier film can be applied to any device having an elastomeric component that requires high barrier properties against water vapor transmission and/or gas (such as oxygen) transmission. Such components can include plunger tips 400 having a barrier film 416 for syringes, tip caps 500 having a barrier film 516 for syringes and sealing disks 600 having a barrier film 616, as shown in FIGS. 15 and 16.

The foregoing methods of manufacturing the elastomeric closure 10 with barrier layer also provide the necessary bonding strength between the barrier film 16 and the elastomeric material of the elastomeric closure 10. However, the inventor has also surprisingly found that the foregoing methods result in elastomeric closures having varying bonding strengths between the barrier film 16 and the top and bottom portions 12, 14, depending upon the specific method of achieving bonding e.g., bonding layers, plasma treating the barrier film, and adhesion promoters, and the particular materials used for the elastomeric closure 10 and the barrier film 16. For example, the use of bonding layers are preferred when forming bromobutyl elastomeric closures with aluminum foil or a polyester/$Al_2O_3$ film, while the use of a plasma treated barrier film is preferred with a silicone elastomeric closure and a polyester/$Al_2O_3$ film.

The following specific non-limiting examples illustrate methods of manufacturing an elastomeric closure with barrier layer in accordance with the present invention.

EXAMPLE 1

Uncured bromobutyl rubber was used as the starting material for molding the top and bottom portions of a bromobutyl elastomeric closure. The uncured bromobutyl rubber was placed within a bottom mold cavity and then a layer of aluminum foil coated with epoxy was placed on top of the uncured bromobutyl rubber. The uncured bromobutyl rubber and aluminum foil was then hot pressed at 180 degrees C. for 4 minutes. The vulcanized bottom portion and aluminum foil was then removed, trimmed and placed in another bottom mold cavity. A second layer of uncured bromobutyl rubber was then placed in a top mold cavity in facing engagement with the exposed surface of the aluminum foil. The second layer of uncured bromobutyl rubber was then hot pressed to the vulcanized bottom portion and aluminum foil to form a unitary structure defining the bromobutyl elastomeric closure, at 180 degrees C. for 6 minutes.

EXAMPLE 2

Uncured bromobutyl rubber was used as the starting material for molding the top and bottom portions of a bromobutyl elastomeric closure. The uncured bromobutyl rubber was placed within a bottom mold cavity and then a barrier film of polyester/$Al_2O_3$ coated with a silane compound was placed on top of the uncured bromobutyl rubber. The uncured bromobutyl rubber and polyester/$Al_2O_3$ film was then hot pressed at 180 degrees C. for 4 minutes. The vulcanized bottom portion and polyester/$Al_2O_3$ film was then removed, trimmed and placed in another bottom mold cavity. A second layer of uncured bromobutyl rubber was then placed in a top mold cavity in facing engagement with the exposed surface of the polyester/$Al_2O_3$ film. The second layer of uncured bromobutyl rubber was then hot pressed to the vulcanized bottom portion and polyester/$Al_2O_3$ film to form a unitary structure defining the bromobutyl elastomeric closure, at 180 degrees C. for 6 minutes.

EXAMPLE 3

Uncured silicone rubber was used as the starting material for molding the top and bottom portions of a silicone elastomeric closure. The uncured silicone rubber was placed within a bottom mold cavity and then a barrier film layer of polyester/$Al_2O_3$ coated with a silane compound was placed on top of the uncured silicone rubber. The uncured silicone rubber and polyester/$Al_2O_3$ film was then hot pressed at 140 degrees C. for 4 minutes. The vulcanized bottom portion and polyester/$Al_2O_3$ film was then removed, trimmed and placed in another bottom mold cavity. A second layer of uncured silicone rubber was then placed in a top mold cavity in facing engagement with the exposed surface of the polyester/$Al_2O_3$ film. The second layer of uncured silicone rubber was then hot pressed to the vulcanized bottom portion and polyester/$Al_2O_3$ film to form a unitary structure defining the silicone elastomeric closure, at 140 degrees C. for 6 minutes.

EXAMPLE 4

Uncured silicone rubber was used as the starting material for molding the top and bottom portions of a silicone elastomeric closure. The barrier film used was a polyester/$Al_2O_3$ film that had been plasma treated on both sides. The uncured silicone rubber was placed within a bottom mold cavity and then the polyester/$Al_2O_3$ barrier film was placed on top of the uncured silicone rubber. The uncured silicone rubber and polyester/$Al_2O_3$ film was then hot pressed at 140 degrees C. for 4 minutes. The vulcanized bottom portion and polyester/$Al_2O_3$ film was then removed, trimmed and placed in another bottom mold cavity. A second layer of uncured silicone rubber was then placed in a top mold cavity in facing engagement with the exposed surface of the polyester/$Al_2O_3$ film. The second layer of uncured silicone rubber was then hot pressed to the vulcanized bottom portion and polyester/$Al_2O_3$ film to form a unitary structure defining the silicon elastomeric closure, at 140 degrees C. for 6 minutes.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as described above.

I claim:
1. An elastomeric closure comprising:
   a top portion having a bottom surface topology comprising:
      a first centrally-positioned, linear-in-cross-section bottom-surface portion;

a second linear-in-cross-section bottom-surface portion disposed axially below and surrounding the first centrally-positioned linear-in-cross-section bottom-surface portion, the second linear-in-cross-section bottom-surface portion angled radially outwardly and downwardly at an angle of about 5 to 25 degrees with respect to the first centrally-positioned, linear-in-cross-section bottom-surface portion;

a first arcuate transition region extending directly between the first and second linear-in-cross-section bottom-surface portions; and a third radially-outwardly-most linear-in-cross-section bottom-surface portion disposed axially below the first linear-in-cross-section bottom-surface portion and disposed axially above the second linear-in-cross-section bottom-surface portion; and a bottom portion disposed axially below the top portion, the bottom portion having a top surface topology comprising:

a first centrally-positioned linear-in-cross-section top-surface portion;

a second linear-in-cross-section top-surface portion disposed axially below and surrounding the first centrally-positioned, linear-in-cross-section top-surface portion, the second linear-in-cross-section top-surface portion angled radially outwardly and downwardly with respect to the first centrally-positioned, linear-in-cross-section top-surface portion terminating in a distal edge defining an outermost perimeter of the bottom portion; and a second arcuate transition region extending directly between the first and second linear-in-cross-section top-surface portions, wherein the first centrally positioned linear-in-cross-section top-surface portion is complementarily shaped to and in register with the first centrally positioned linear-in-cross-section bottom-surface portion, the second linear-in-cross-section top-surface portion is complimentarily shaped to and in register with the second linear-in-cross-section bottom-surface portion, and the top surface of the bottom portion faces the bottom surface of the top portion; and a barrier film located between the bottom surface of the top portion and the top surface of the bottom portion, wherein the barrier film extends substantially completely across one of the top surface of the bottom portion and the bottom surface of the top portion, and the bottom portion and the top portion encapsulate the barrier film or are flush with exposed surfaces of the barrier film.

2. The elastomeric closure of claim 1, wherein the barrier film is selected from the group consisting of a metallic foil and a polymeric film.

3. The elastomeric closure of claim 1, wherein the barrier film is aluminum foil.

4. The elastomeric closure of claim 1, wherein the barrier film is selected from the group consisting of a polyester film, a polyamide film, a polyvinylchloride film, a polychlorotrifluorethylene film, a halogenated polymer film, a non-halogenated polyisobutylene-isoprene rubber film, a polyvinylidene chloride film, a cyclic olefin copolymer film, a polypropylene film, a polyethylene film, a polytetrafluoroethylene film, a silicone oxide coated polymer film, an aluminum oxide coated polymer film, and combinations thereof.

5. The elastomeric closure of claim 1, wherein the barrier film is a plasma treated barrier film.

6. The elastomeric closure of claim 1, further comprising a first bonding layer between the bottom portion and the barrier film, and a second bonding layer between the top portion and the barrier film.

7. The elastomeric closure of claim 6, wherein at least one of the first bonding layer and the second bonding layer is selected from the group consisting of a silane compound, a resin based primer, an epoxy, $SiO_2$, $Al_2O_3$, and a diamond-like carbon.

8. The elastomeric closure of claim 1, wherein the elastomeric closure is one of a stopper, a syringe piston, a syringe tip cap, and a sealing disk.

9. The elastomeric closure of claim 1, wherein each of the top portion and the bottom portion of the elastomeric closure includes an adhesion promoter.

10. The elastomeric closure of claim 9, wherein the adhesion promoter is selected from the group consisting of a silane compound, an epoxy, and a polymer resin.

11. A method of manufacturing the elastomeric closure of claim 6, comprising:

plasma treating a top surface and a bottom surface of the barrier film to increase its surface energy;

layering the plasma treated barrier film on a first layer of uncured elastomer;

hot pressing and vulcanizing the plasma treated barrier film and the first layer of uncured elastomer together to form the bottom portion of the elastomeric closure bonded to the plasma treated barrier film; and hot pressing and vulcanizing the bottom portion of the elastomeric closure bonded to the plasma treated barrier film to a second layer of uncured elastomer to form the top portion of the elastomeric closure bonded to the plasma treated barrier film.

12. The method of claim 11, wherein the top portion and the bottom portion is formed from silicone rubber and the barrier film is a polyester/$Al_2O_3$ film.

13. The method of claim 11, wherein the hot pressing step includes temperature of about 140 to 220 degrees Celsius and pressures of about 40 to 70 kg/cm$^2$ for about 2 to 15 minutes.

14. A method of manufacturing the elastomeric closure of claim 6, comprising:

forming the first bonding layer and the second bonding layer on the barrier film;

layering the barrier film on a first layer of uncured elastomer;

hot pressing and vulcanizing the barrier film and the first layer of uncured elastomer together to form the bottom portion of the elastomeric closure bonded to the barrier film; and hot pressing and vulcanizing the bottom portion of the elastomeric closure bonded to the barrier film to a second layer of uncured elastomer to form the top portion of the elastomeric closure bonded to the barrier film.

15. The method of claim 14, wherein the top portion and the bottom portion is formed from bromobutyl rubber or silicone rubber, the barrier film is aluminum foil or a polyester/$Al_2O_3$ film, and the bonding layer is an epoxy or silane compound.

16. The method of claim 14, wherein each of the first bonding layer and the second bonding layer is $SiO_2$, $Al_2O_3$, or a diamond-like carbon each formed by plasma enhanced chemical vapor deposition.

17. A method of manufacturing the elastomeric closure of claim 9, comprising:
- mixing uncured elastomer with an adhesion promoter;
- layering the barrier film on a first layer of uncured elastomer with adhesion promoter;
- hot pressing and vulcanizing the barrier film and the first layer of uncured elastomer with adhesion promoter together to form the bottom portion of the elastomeric closure bonded to the barrier film; and
- hot pressing and vulcanizing the bottom portion of the elastomeric closure bonded to the barrier film to a second layer of uncured elastomer with adhesion promoter to form the top portion of the elastomeric closure bonded to the barrier film.

18. The method of claim 17, wherein the adhesion promoter is selected from the group consisting of a silane compound, an epoxy, a polymer resin, and an adhesive.

* * * * *